(12) United States Patent
Visweswara et al.

(10) Patent No.: US 12,193,843 B2
(45) Date of Patent: Jan. 14, 2025

(54) ON-BODY SENSOR SYSTEM AND METHOD

(71) Applicant: KONINKLIJKE PHILIPS N.V., Eindhoven (NL)

(72) Inventors: Ashoka Sathanur Visweswara, Amstelveen (NL); Mohammed Meftah, Tilburg (NL); Mark Thomas Johnson, Arendonk (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 17/254,912

(22) PCT Filed: Jun. 25, 2019

(86) PCT No.: PCT/EP2019/066759
§ 371 (c)(1),
(2) Date: Dec. 22, 2020

(87) PCT Pub. No.: WO2020/002290
PCT Pub. Date: Jan. 2, 2020

(65) Prior Publication Data
US 2021/0259633 A1 Aug. 26, 2021

Related U.S. Application Data

(60) Provisional application No. 62/691,243, filed on Jun. 28, 2018.

(51) Int. Cl.
*A61B 5/00* (2006.01)
*A61B 5/06* (2006.01)

(52) U.S. Cl.
CPC ............ *A61B 5/684* (2013.01); *A61B 5/0028* (2013.01); *A61B 5/061* (2013.01); *A61B 5/6833* (2013.01); *A61B 2560/04* (2013.01)

(58) Field of Classification Search
CPC ... A61B 2560/04; A61B 5/0028; A61B 5/061; A61B 5/062; A61B 5/6833; A61B 5/684
See application file for complete search history.

(56) References Cited

U.S. PATENT DOCUMENTS

| | | |
|---|---|---|
| 2005/0080334 A1 | 4/2005 | Willis |
| 2011/0270237 A1 | 11/2011 | Werneth et al. |
| 2017/0086023 A1 | 3/2017 | Tartz et al. |

FOREIGN PATENT DOCUMENTS

WO 2017167887 A1 10/2017

OTHER PUBLICATIONS

International Search Report and Written Opinion, International Application No. PCT/EP2019/066759, Mailed on Sep. 11, 2019.

(Continued)

*Primary Examiner* — Amanda K Hulbert

(57) ABSTRACT

An on-body sensing system (30) comprises a plurality of skin interface elements for coupling electrical signals to and from the body. The system is adapted to derive an indication of a position of at least one positionable interface unit (32) based on transmission of signals between the positionable unit and a set of spatially separated reference units (34), the reference units being positioned at a set of known locations on the body. Transmitted signals are sensed at multiple pairs (52) of electrodes on each reference unit and signal characteristics derived for each pair, and based on this a direction of arrival of the signal determined. By collating all of the measured arrival angles, and by reference to a reference dataset containing information indicative of known signal arrival angles when signals are transmitted internally between the reference units themselves, an indication of position of the positionable unit is derived.

14 Claims, 8 Drawing Sheets

(56) References Cited

OTHER PUBLICATIONS

Cho, N. et al., "The Human Body Characteristics as a Signal Transmission Medium for Intrabody Communication", IEEE Transactions on Microwave Theory and Techniques, vol. 55, No. 5, May 2007.

Zhang, Y. et al., "SkinTrack: Using the Body as an Electrical Waveguide for Continuous Finger Tracking on the Skin", Carnegie Mellon University, 2016.

Dash, S. et al., "A Survey on Localization in Wireless Sensor Network by Angle of Arrival", IJIRST—International Journal for Innovative Research in Science & Technology| vol. 2 | Issue 04 | Sep. 2015.

Grant S. Anderson, C. G. (2013). Body Coupled Communication: The Channel and Implantable Sensors. IEEE Body Sensor Networks.

Joonsung Bae, e. (2012). The Signal Transmission Mechanism on the Surface of Human Body for Body Channel Communication. IEEE Transactions on Microwave Theory and Techniques.

Maicon D. Pereira, e. (2015). Characterization and Modelling of the Capacitive HBC Channel. IEEE Transactions on Instrumentation and Measuremen.

Sangkil, e. (2014). Ambient RF Energy Harvesting Technologies for Self-Sustainable Standalone Wireless Sensors Platforms. IEEE Micro.

Technologies, D. (2015). RF Energy Harvesting for the Low Energy Internet of Things.

ON-BODY SENSOR SYSTEM AND METHOD

This application is the U.S. National Phase application under 35 U.S.C. § 371 of International Application No. PCT/EP2019/066759, filed on 25 Jun. 2019, which claims the benefit of U.S. Provisional Application No. 62/691,243, filed 28 Jun. 2018. These applications are hereby incorporated by reference herein.

FIELD OF THE INVENTION

The embodiments described herein may relate to an on-body sensor system having one or more on-body sensor elements, and a method for configuring the same.

BACKGROUND OF THE INVENTION

On-body sensing systems permit accurate long-term monitoring of physiological parameters of a subject. On-body systems are based on use of wearable devices or units, including for instance patches, which are attached to or mountable on the body and maintain a relatively stable position over time. By electrically interfacing with the skin or body, vital signs or other parameters may be monitored.

On-body systems may typically be used in low acuity settings such as a general ward and also at a subject's home. Improved reliability in physiological parameter monitoring in general wards is needed to reduce mortality rates, by enabling detection of any deterioration in condition as early as possible. The capacity to monitor reliably at a subject's home also permits earlier discharge of patients without risk of undetected deterioration. Monitoring will typically continue up to 30 days from discharge for example.

In the case of patches, in many cases these need to be changed every 2-3 days because of depleted battery charge, degradation of adhesion and/or skin irritation. As a result, it falls to a patient him- or herself and/or an informal caregiver such as a relative to replace and re-attach the patch. In some cases, the patch has to be moved to other locations and orientations. Accurate placement of the patch upon replacement is important to ensure that physiological parameters are correctly determined.

Similarly, accurate placement is imperative for handheld devices that are in contact with the body such as handheld imaging sensors and/or devices. For example, accurate placement of a handheld ultrasound device that may include capacitive micromachined ultrasonic transducer (cMUT) arrays for image acquisition is essential for the registration of the correct physiological images. Accordingly, systems, methods, and/or devices to ensure proper placement (orientation and positioning) of any sensor-related device is desirable.

Academic work has previously described an electrical field model of the human body. The model may be used to determine the frequency response of the human body as a signal transmission medium. It may be measured by generating and capacitively coupling an electrical signal having a known frequency and amplitude at one point on the human body. The coupled signal may be then sensed and measured at a different, remote point on the body by a sensor. The received signal may be analyzed and various signal properties derived. This process may be repeated for multiple different signals having different transmitter frequencies and also for various distances and body locations of the on-body sensing element relative to the transmitting location.

One example model is presented in Namjum Cho, et al. (2007). The Human Body Characteristics as a Signal Transmission Medium for Intrabody Communication. *IEEE Transactions on Microwave Theory and Techniques*. In this paper, the authors propose a near-field coupling model of the human body based on modelling the human body in terms of three cylinders: two for the arms and one for the human torso. This is illustrated in FIG. 1.

As shown in FIG. 1(*a*), the arms and the human torso are segmented with 10 cm long unit blocks, each with resistances and capacitances. The arms and the torso are together modelled as distributed RC network as shown in FIG. 1(*b*). In a similar manner, a human leg may be modelled with corresponding resistances and impedances. The arm model has resistance and capacitance with subscript "A" and the torso has resistance and capacitance with subscript "T".

One practical implementation of the signal transmission and sensing approach is presented in Zhang, Y. et al, 2016, May. "Skintrack: Using the body as an electrical waveguide for continuous finger tracking on the skin". In Proceedings of the 2016 CHI Conference on Human Factors in Computing Systems (pp. 1491-1503).

This paper proposes a continuous finger tracking technology called SkinTrack. SkinTrack is a wearable system that enables continuous touch tracking across the skin. The system comprises a ring, which emits a continuous high-frequency AC signal, and a sensing wristband embodying multiple sensor electrodes. Due to the phase delay inherent in propagating the high frequency AC signal through the body, a phase difference may be observed between pairs of electrodes. The SkinTrack system measures these phase differences to compute a 2D coordinate location of the subject's finger touching on their skin. The resolution (i.e. accuracy) of SkinTrack method is approximately 7 mm.

The same paper describes a method whereby the phase angle difference between the sensed signals at two different locations on the human body is used as a measure of localization of the signal transmitter with respect to the sensors. FIG. 2 schematically illustrates the technique, where the transmitter is in the form of a ring 12. The location of the transmitter relative to two sensor electrodes 14*a*, 14*b* on a smartwatch is identified using the technique.

When an 80 MHz RF signal is used, the wavelength of the electromagnetic wave propagating through the human body is around 91 cm. This results in phase angle difference of approximately 4°/cm for one single cycle of the wave. If the localization is performed within one wavelength of the RF signal (i.e. within around 91 cm), then it is possible to derive an indication of the position of the transmitter with relative to the two sensors by measuring the phase angle difference between the two received signals.

When monitoring physiological parameters, accurate placement of patches is critical for correct functioning. And when using various other sensing devices, such as the handheld imaging sensor devices described herein, placement of the device is essential for correct results. However, in the home-based monitoring and other regimes described above, the patient, a non-clinician caregiver, and/or a medical professional is required to place the patches her- or himself. This may be challenging, even with medical training, and especially without medical training, and even more so for patients having, for example, poor eyesight, dexterity, or having reduced cognitive function. A solution to facilitate reliable placement of a patch and/or other sensing device as described herein at a correct location (e.g. positioning and orientation) would therefore be of value, to increase reliability of monitoring, sensing, and/or imaging.

SUMMARY OF THE INVENTION

According to examples in accordance with an aspect of the invention, there is provided an on-body sensor system, comprising:
- a plurality of skin interface units for coupling electrical signals into and/or out of the body of a subject, including two or more reference units, each for placement against a respective known region of the skin, and at least one positionable unit for placement at a further unknown position, each of the reference units comprising at least two pairs of skin coupling electrodes; and
- a controller operably coupled with the skin interface units and adapted to
    - control transmission of signals through the body between the positionable unit and the reference units,
    - derive at each reference unit one or more signal characteristics associated with signals received at each pair of electrodes respectively of the unit, and based on this derive an indication of an angle of arrival of signals at the reference unit,
    - access a reference dataset comprising information indicative of known angles of arrival of signals at reference units if placed at said known regions of the skin, and if received from locations corresponding to one or more of said other known regions of the skin, and
    - derive an indication of position of the at least one positionable unit based on the derived angles of arrival of signals and on the information in the reference dataset, and generate output information based on the derived indication of position.

The various embodiments described herein may be based on determining the position of a skin interface unit (for example a patch or a handheld device) based on an analysis of the angles at which various signals propagated from the interface unit are sensed as arriving at a number of reference units of known position. This information may be used in combination with reference information corresponding to known signal arrival angles for signals if transmitted internally between locations of various pairs of reference units to thereby determine a position of the positionable unit. This may be used to facilitate accurate positioning of the unit on the body for reliable on-body sensing of for instance physiological parameters using the unit.

The reference units are placed in known locations on the body, these being locations to which the reference data may be calibrated. The reference dataset effectively permits mapping between the derived signal angle measurements for the positionable unit, and its position in real space. The derived angles may be related or compared or resolved with respect to the angle-related information of the dataset, allowing a position of the positionable unit with respect to the reference units to be calculated. Using the known locations of the devices in real space, this then allows determination of the real position of the positionable unit. The dataset acts as a map between signal space and real-space.

Accordingly, the reference information may provide a mapping tool for mapping the signal angle information for the positionable unit into position information. The reference dataset may take the form of a device position map for the reference units.

Each reference unit has at least two pairs of electrodes. The electrodes of each pair are spatially separated. Separate sets of one or more signal characteristics are derived in respect of signals received at each respective pair. This gives one set of signal characteristics for each separate electrode pair. This permits angle of arrival to be determined, since the disparity in the measured or computed characteristics at the two pairs allows information about signal propagation direction to be derived. For instance if propagation velocity may be known, the different arrival times at the two electrode pairs allow a propagation direction to be determined based on the known separation between the pairs.

The system may advantageously be for monitoring one or more physiological parameters of a subject and/or obtaining other sensed data or imaging data of a subject. The positionable unit may in this case be for use in sensing the one or more physiological parameters or obtaining imaging data. By permitting a position of the positionable unit to be determined, it may be checked whether it is correctly placed for achieving accurate or reliable physiological parameter readings or correct image data.

The electrical signals are electrical stimuli applied to the skin or body. They are carried or transported by the body through electrical body channels. They may be AC signals. The signals may be capacitively coupled into the body, or inductively coupled into the body. The same or a different coupling mechanism may be used to couple signals out of the body for sensing.

Advantageously, the signals generated for coupling into the body are in the RF frequency range 10 MHz to 150 MHz since in this frequency range the body acts as a waveguide for signal transmission.

The system comprises skin interface units for electrically coupling signals into and back from the skin or body. Each unit may be for mounting or applying against the skin, either in contact with the skin or in close proximity to it, possibly separated by a small clearance or space.

One or more of the skin interface units may comprise or consist of a pad, e.g. a patch, for mounting against the skin. One or more of the skin interface units may comprise or consist of a wearable device, for instance shaped or configured to fit to a particular part of the body for mounting against the skin of that part. They may be on-body units in the sense of being coupled or attached the body fixedly or may be off-body units in the sense of being for temporary placement against a region of the skin, for instance a weight scale for placement against the skin of the foot by standing on the scale. One or more of the skin interface units may comprise or consist of a handheld device, for instance handheld imaging sensors and/or devices.

Optionally, the controller may generate signals and the transmitter unit controlled to apply these signals to the body. The transmitter unit itself comprises means (e.g. circuitry) to generate the signals.

The controller referred to above may include a dedicated controller as part of the system and/or a controller as part of the units described herein. A controller may be a distributed controller in the sense that one or all of the control functions associated with it may be implemented by other components of the system, e.g. the control function may be distributed between multiple components. For example, the skin interface units may perform one or more of the control functions. For example the reference units may perform signal processing to derive the signal characteristics.

The indication of position of the positionable unit may refer to a positioning on the body, a portion of the body, or on the skin. Position may mean an absolute position, i.e. a location on the body, or may mean a relative position, i.e. relative to the reference units, e.g. a distance or separation from the reference units.

The controller may be adapted to further derive an indication of orientation of the positionable unit.

In this case, the positionable unit may comprise a plurality of pairs of skin coupling electrodes. By using a plurality of pairs of electrodes, this may facilitate a convenient means of deriving orientation. In summary, this may be based on iteratively transmitting signals between each of the multiple pairs of electrodes of the positionable unit and the electrode pairs of the two or more reference units. Signal characteristics associated with signals sent between each of the positionable unit electrode pairs' and each of the reference units' electrodes may then be derived. Angles of arrival of signals from each of the positionable unit electrode pairs at each of the electrode pairs of the two or more reference units may also be derived.

The complete set of signal characteristics for the multiple positionable unit electrode pairs, and/or the complete set of arrival angles for the multiple positionable unit electrode pairs, may then be derived. This set may provide a unique characterization of orientation of the positionable unit and may be used to identify the orientation of the positionable unit. The reference dataset may include known sets of these characteristics and/or arrival angles and their associated orientations, and orientation may be derived based on comparing a derived set with these known sets.

Orientation may mean an orientation relative to the skin or portion of the body or an absolute orientation (e.g. measured using a gravity sensor and/or compass).

The derived indication of position may be a direct or indirect indication of position. It may be quantitative co-ordinate position for instance. It may be in terms of the reference positions, e.g. it may be an indication of a reference position to which the current position corresponds, or to which it is close.

The dataset may be stored locally, e.g. in a memory comprised by the system, e.g. by the controller. The dataset may be stored remotely, e.g. in the cloud, or on a remote computer with which the controller may be communicable.

The at least one positionable unit may be at least adapted for coupling signals into the body for performing a signal transmission function. The reference units are at least adapted for coupling signals out of the body for performing a signal receiving function. The reference units may be operable to perform both a transmission and receiving function. This allows them to be used in performing a calibration procedure by which the reference dataset may be constructed. This will be discussed in more detail below.

The one or more signal characteristics determined for each electrode pair may include at least one of: phase angle, signal transmission time, and signal attenuation between transmission and receipt. Transmission time means signal time of flight: propagation duration between initial transmission and receipt. Signal attenuation means signal path loss: change in signal strength between initial transmission and receipt.

Each reference unit comprises at least three pairs of skin-coupling electrodes, and preferably at least four pairs of skin coupling electrodes.

Using more than two pairs of electrodes allows a more precise indication of signal arrival angle to be derived. Two electrode pairs allows only a 180° scope of precision, i.e. it may be determined at what angle the signal arrives relative to a notional horizontal of the reference unit, from 0-180°, but not whether it arrives from the front or the back of the unit.

Using three electrode pairs extends the scope of precision to 360°, allowing the angle of arrival from 0-360° to be uniquely determined. Four electrode pairs further improves the resolution of the angle measurement.

Advantageously, for each reference unit the controller may be adapted to determine at least one differential signal characteristic value based on a difference in the value of a signal characteristic between two of the pairs of electrodes. This differential value will differ depending on the angle of arrival of the signal. Hence, as noted above, this information may be used for determining the angle of arrival of the signal, for instance in combination with known separation distance between the electrode pairs and known signal propagation speed.

In certain examples, for each reference unit, and for at least one signal characteristic, a differential signal characteristic value may be calculated between each electrode pair and each other electrode pair comprised by the receiver, to thereby form a set of differential values.

Where more than two electrode pairs are included, the consequently derived set of differential values provides a unique characterization of the signal angle of arrival. Optionally, the set of values may be arranged or represented in the form a differential matrix.

Advantageously, the derived set of differential values may be normalized by dividing each value in the set by the maximum differential value contained in the set. The normalization ensures that the set of differential values may be directly mapped to reference sets of differential values, regardless of the particular dimensions or operating parameters of the system. This allows measured values to be easily compared with reference values, optionally permitting derivation of an angle of arrival by reference to said reference values.

Determining the angle of arrival may in particular comprise comparing the derived set of differential values with a dataset of pre-determined sets of differential values, each pre-determined set corresponding to a known signal angle of arrival. Thus the derived set of differential values may be mapped to a corresponding signal angle of arrival. Note that this dataset of pre-determined differential values may be different to the reference dataset defined above which latter dataset may be for determining a position indication once angle of arrival has already been determined.

With regards to this latter reference data set, the reference dataset may according to certain embodiments comprise or consist of a device body map for the reference units, representative of relative positioning of the reference units on the body. The body map may be representative of relative body positions of the reference units, for instance as characterized or indicated by signal arrival angles (i.e. relative angular positioning) and preferably also separation distances (e.g. as indicated from relative signal arrival times). The device body map may be represented in the form of co-ordinate positions of the reference units on the body (from which relative angle information may be implicit or may be derived) or may simply be represented in terms of a list of relative distances and angles of each reference unit to each other reference unit. The co-ordinate positions in this case may be in terms of a local body co-ordinate system, e.g., a co-ordinate system of a body 'reference frame'.

In examples, the indication of position may be determined based on a triangulation technique. For instance, triangulation between the derived angles of arrival and the pre-determined reference angles of arrival.

The positionable unit may comprise more than one pair of electrodes. The controller may be configured to identify the number of electrode pairs comprised by the positionable unit, and to control transmission of signals by each electrode pair in turn to each of the reference units, and to derive at each reference unit a separate set of signal characteristics associated with the signals transmitted from each electrode pair.

Including multiple pairs of electrodes in the positionable unit may permit the angle of arrival of signals at the reference units, and in addition its position, to be more precisely characterized and determined.

In addition, and as noted above, including multiple pairs of electrodes in the positionable unit may provide a convenient means of deriving an orientation of the positionable unit, based on sensing signal characteristics for signals sent from each of the multiple pairs of electrodes in turn. The full set may provide a characterization of angle of orientation of the positionable unit.

Each of the reference units may optionally be operable as both a signal transmitter and signal receiver. This may allow the reference units to be used for performing an initial calibration procedure for initially compiling the reference dataset of signal angle-of-arrival information. This involves transmission of signals between the reference units.

A further aspect of the various embodiments described herein may include a method of calibrating an on-body sensor system for determining position of a skin interface unit of the system, the system comprising
  a plurality of skin interface units for coupling electrical signals into and/or out of the body of a subject, including two or more reference units, each for placement against a respective known region of the skin, and at least one positionable unit for placement at a further unknown position, each of the reference units comprising at least two pairs of skin coupling electrodes,
the method comprising:
positioning the two or more reference units against said respective known regions of the skin;
sequentially controlling each of the reference units to transmit signals into the body toward the other reference units, and in each case deriving at one or more other reference units one or more signal characteristics associated with signals received at each electrode pair respectively of the unit, and deriving based on this an indication of an angle of arrival of the signals at each of said other reference units;
generating and storing a dataset of information indicative of the derived angles of arrival of signals transmitted between the reference units, the dataset for use as a reference in subsequently deriving indications of position of the at least one positionable unit based on angles of arrival of signals transmitted between the positionable unit and the reference units.

In certain examples, the sequential control step comprises in each case deriving at each of the other reference units one or more signal characteristics associated with signals received at each electrode pair respectively of the other unit, and deriving based on this an indication of an angle of arrival of the signals at each of said reference units Various embodiments described herein may include a method of determining placement of skin interface units of an on-body sensing system, the system comprising:
  a plurality of skin interface units for coupling electrical signals into and/or out of the body of a subject, including two or more reference units, each for placement against a respective known region of the skin, and at least one positionable unit for placement at a further unknown position, each of the reference units comprising at least two pairs of skin coupling electrodes; and the method comprising:
controlling transmission of signals through the body between the positionable unit and the reference units,
deriving at each reference unit one or more signal characteristics associated with signals received at each pair of electrodes respectively of the unit, and based on this deriving an indication of an angle of arrival of the signals at the reference unit;
accessing a reference dataset comprising information indicative of known angles of arrival of signals at reference units if placed at said known regions of the skin, and if received from locations corresponding to one or more of said other known regions of the skin; and
deriving an indication of position of the at least one positionable unit based on the derived angles of arrival of signals and on the information in the reference dataset, and generating output information based on the derived indication of position.

Options, examples and variations outlined above in relation to the system-related embodiments described herein may be applied equally to the above method-related embodiments.

For example, the method may in certain examples further comprise determining at least one differential signal characteristic value based on a difference in the value of a signal characteristic between two of the pairs of electrodes.

The method may comprise, for each reference unit, and for at least one signal characteristic, calculating a differential signal characteristic value between each electrode pair and each other electrode pair comprised by the reference unit, to thereby form a set of differential values.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1A:
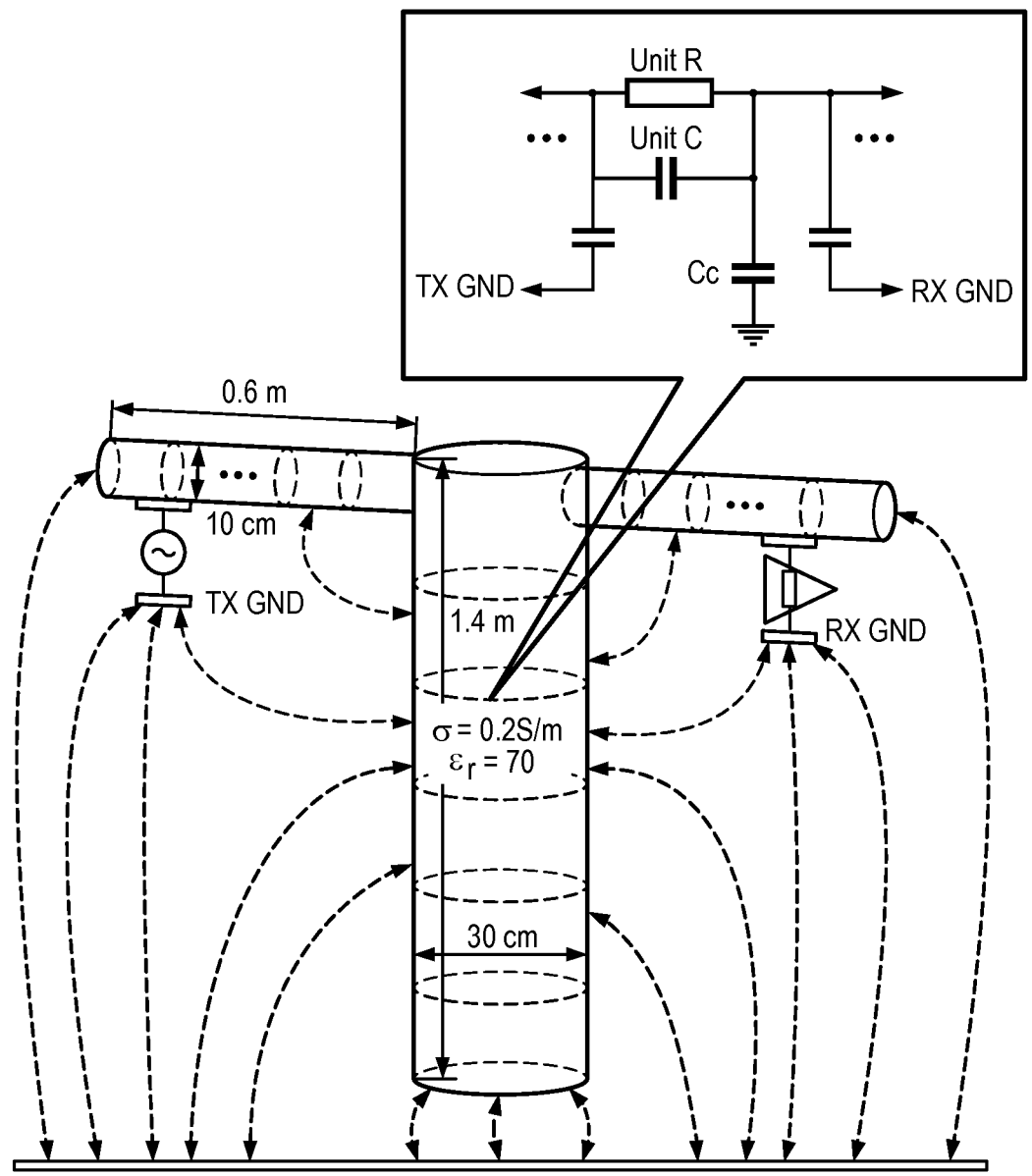
FIGS. 1(a) and (b) schematically depict a near field coupling model of the human body according to the prior art.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods described herein may become better understood from the following description, appended claims, and accompanying drawings. It should be understood that the Figures are merely schematic and are not drawn to scale. It should also be understood that the same reference numerals are used throughout the Figures to indicate the same or similar parts.

The embodiment(s) described herein may provide an on-body sensing system comprising a plurality of skin interface elements for coupling electrical signals to and from the body. The system may be adapted to derive an indication of a position of at least one positionable interface unit based on transmission of signals between the positionable unit and a set of spatially separated reference units, the reference units being positioned at a set of known locations on the body. Transmitted signals are sensed at multiple pairs of electrodes on each reference unit and signal characteristics derived for each pair, and based on this a direction of arrival of the signal determined. By collating all of the measured arrival angles, and by reference to a reference dataset containing information indicative of known signal arrival angles when signals are transmitted internally between of the reference units themselves, an indication of position of the positionable unit may be derived.

The systems, devices, and/or methods described herein may allow an on-body sensor unit, for example for monitoring one or more physiological parameters, to continue to be used for an extended period by a patient at home after being discharged. A sensor element (for instance a sensor patch) of such a system for instance will often need to be replaced on a regular basis. When the patient positions the new patch, they may position it inaccurately. Embodiments of the present system may determine an indication of position of the sensor element. This may be used to assist accurate placement for reliable monitoring.

The systems, devices, and/or methods described herein may allow a handheld sensing or imaging-related device to provide more accurate imaging data. For example, using the systems, devices, and/or methods described herein may provide accurate placement of a handheld ultrasound device that may include capacitive micromachined ultrasonic transducer (cMUT) arrays for image acquisition which may be essential for the registration of the correct physiological images.

The embodiments described herein are based on using derived angles of arrival of signals at a set of multiple reference units of known position, to derive an indication of position of a positionable unit, for instance a sensor patch, by reference to a reference dataset of known angle information for the reference units.

Figure 3:
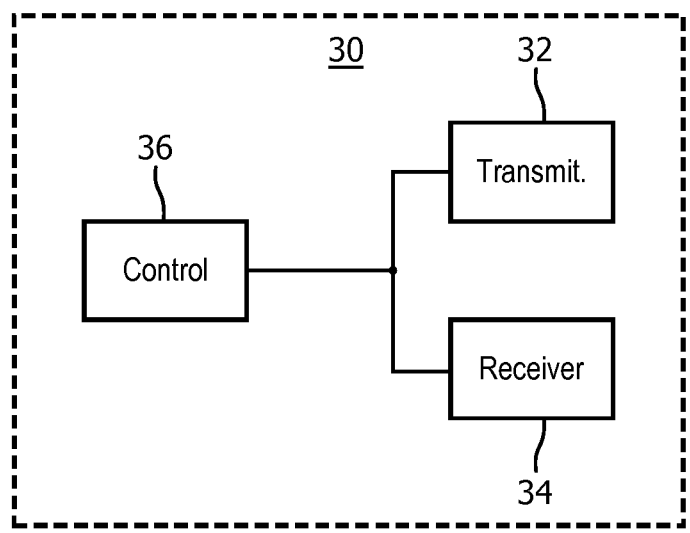
FIG. 3 shows in block diagram form an example system in accordance with one or more embodiments.

FIG. 3 schematically depicts in block diagram form an example on-body sensing system 30 in accordance with one or more embodiments. The system comprises a plurality of skin interface units 32, 34a, 34b for coupling electrical signals into and/or out of the body of a subject. The skin interface units include two reference units 34 for placement against respective know regions of the skin of a subject, and one positionable unit 32 for placement at a further unknown position on the body.

Figure 1B:
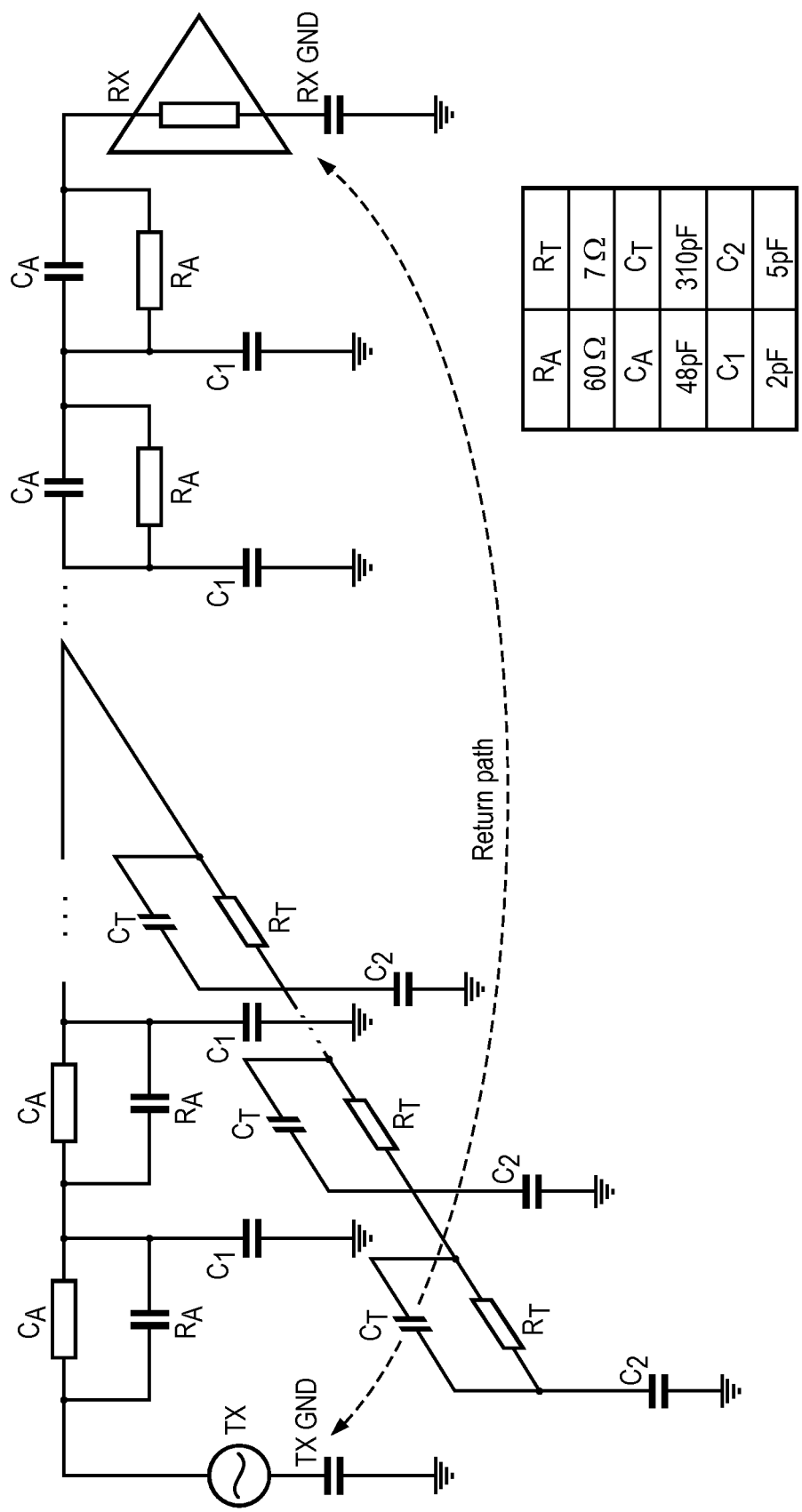
Figure 2:
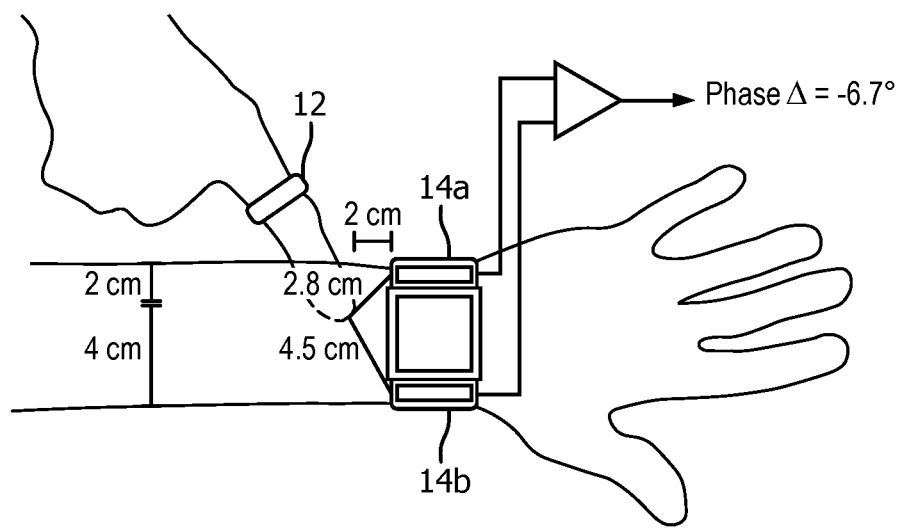
FIG. 2 schematically depicts a prior art technique for determining on-body position based on body-transmitted AC signals.

It noted that although the example of FIG. 1 comprises a single positionable unit 32, in further examples more than one positionable unit may be included in the system 30. Likewise, more than two reference units may be included. A greater number of reference units may provide more precise position determination.

Each of the reference units 34a, 34b comprises two pairs 52a, 52b of electrodes. For simplicity, the electrode pairs are schematically depicted as single squares with the individual electrodes of each pair not visible. The pairs of electrodes are spatially separated from one another. Their position within the unit is shown only schematically; their true position within the unit may vary. More than two pairs of electrodes may be included in each reference unit in alternative examples.

The positionable unit 32 comprises a single pair 52 of electrodes. In further examples more than one pair of electrodes may be included. Again, its position within the unit is shown schematically and true position within the unit may vary.

The shown relative positioning of the positionable unit 32 and reference units 34 in FIG. 3 is schematic only.

The system 30 further comprises a controller 36 operatively coupled with the positionable unit 32 and the reference units 34a, 34b for controlling the units in transmitting and receiving signals respectively. The controller may be connected to the reference and positionable units by any suitable communication means. The connection may be preferably a wireless connection but the embodiments may not be limited to wireless connection. Example communication modes for wireless connection include for example Bluetooth, Wi-Fi, body-coupled communication and ultra wide band communication. Other communication modes and technologies may be used as will be apparent to the skilled person.

Although the system is defined as comprising a separate control unit 36, the controller may in fact be one of the skin interface units in one or more examples, the relevant unit being configured to perform the control functions associated with the controller. Which unit acts as controller may be determined by the system in an initial configuration step for example. In advantageous examples, one of the reference units may configured at the control unit. References to the controller in this disclosure may therefore be understood as referring either to a central controller or a controller as implemented by one of the skin interface units.

Where one of the skin interface units is the control unit, the skin interface units may be operably coupled to one another using for example one of the example communication means outlined above.

The controller 36 may be operable in at least a control mode to carry out a localization procedure for determining an indication of position of the positionable unit. In performing this localization procedure, the controller may be adapted to carry out the following steps:

control transmission of signals through the body between the positionable unit 32 and the reference units 34a, 34b, derive at each reference unit 34 one or more signal characteristics associated with signals received at each pair of electrodes 52 respectively of the unit, and based on this derive an indication of an angle of arrival of signals at the reference unit, access a reference dataset comprising information indicative of known angles of arrival of signals at reference units if placed at said known regions of the skin, and if received from locations corresponding to one or more of said other known regions of the skin, and derive an indication of position of the at least one positionable unit based on the derived angles of arrival of signals and on the information in the reference dataset, and generate output information based on the derived indication of position.

When the localization procedure is performed, the reference units may be assumed to have been positioned against said known regions of the skin of the body.

To facilitate the transmission of signals by the positionable unit, the positionable unit may comprise signal generating means for generating body channel signals for coupling into the body. Body channel signals means signals for transmission through electrical channels of the body.

The positionable unit may comprise a body channel signal transceiver unit operable to both generate and sense signals. This will be described in greater detail to follow. The reference units may each comprise such a transceiver also.

According to certain examples, each of the skin interface units 32, 34a, 34b may be selectably configurable to perform either a signal sensing function or a signal transmitting function. In this example the reference units and positionable unit may be functionally interchangeable, providing a flexibility whereby any unit may perform either the reference unit function or the positionable unit function. Across the lifetime of the device, and over multiple iterations of its use, this flexibility may be valuable. Calibration may need to be performed each time the functions of units are switched. Calibration methods will be described below.

In some examples, a central controller 36 may generate the signals and communicate these to the positionable unit for coupling into the body. However, this may not be practicable in some cases, in particular where there is no wired connection between a central controller and the positionable unit.

The positionable unit may comprise more than one pair of electrodes. In this case, the controller 36 may be adapted to sequentially control each electrode pair in turn to transmit signals. The reference units in this case may derive separate sets of one or more signal characteristics for the signals of each transmitting electrode pair.

Advantageously, the controller may be configured to identify the number of electrode pairs comprised by the positionable unit and to control the transmission of signals by each electrode pair in turn in the case that more than one pair is detected. This allows the system to adapt to any particular positionable unit.

The skin interface units 32, 34 may take different forms.

The positionable unit 32 may be preferably an on-body unit for mounting against the skin of the subject.

Preferably, the positionable unit 32 may be in the form of a sensor patch or pad for mounting against the skin of the subject. The sensor patch may comprise a flexible electrode set for coupling electrical signals into the skin or body. The patch may have an adhesive layer for coupling the patch to the skin.

The positionable unit 32 may be used in monitoring one or more physiological parameters as part of a physiological parameter monitoring function of the system 30. The physiological parameters may be vital signs for instance. Although depicted as a chest-positioned unit 32, the positionable unit 32 may be located in any number of positions relative to the body and/or may be used for accurate placement of, for example, image acquisitions for the registrations of physiological images.

According to one or more examples, one or more of the skin interface units, for example one or more of the reference units 34, may be in the form of a wearable unit configured for mounting or adhesion to a particular part of the body. In advantageous examples, one or more of the reference units may be in the form of a wrist-mountable device. This carries the advantage that the position of the respective reference unit in this case is stable and reliably known. However, this effect could also be achieved with other body-mounted devices that may be fixedly secured to a part of the body, e.g. a chest strap, ankle band, handheld device, or ear hook by way of example.

One or more of the reference units 34 may be in the form of a smart watch device in examples. The smart watch device may comprise the controller 36 according to examples.

One of the reference units may in some examples take the form of an off-body unit such as a weight scale or handheld device having electrodes mounted on an exposed surface arranged for electrical coupling with skin. For example, in the case of a weight scale or other device, the electrodes may be mounted on an exposed upper surface of the unit for electrical coupling with the skin.

In some examples, the output information generated by the controller 36 may be guidance information for guiding a user in positioning the positionable unit 32 at a defined target location.

The output information may comprise a representation or indication of the derived position indication.

Output information may be communicated from the controller to a user output means, for example a sensory output means, for communication to a user. The sensory output means may for instance be a display and/or a speaker.

Where the output information is guidance information, the controller 36 may be configured to compare the derived indication of position with a defined target, and to generate guidance information based on said comparison, for guiding the user in positioning the positionable unit at the target position.

The target position may be pre-programmed. For example, it may be one of a pre-determined set of positions known to provide accurate monitoring of physiological parameters of interest using the positionable unit 32. The target position may be at least partially user-defined, for example via a user input means. For example, the target position may be input by a clinician before a patient leaves hospital, or one of a set of pre-defined target positions may be selected.

The one or more derived signal characteristics may include by way of example phase angle, signal transmission time, and signal attenuation between transmission and receipt. Transmission time means signal time of flight: propagation duration between initial transmission and receipt. Signal attenuation means signal path loss: change in signal strength between initial transmission and receipt. The signal attenuation, or path loss PL, of a signal between transmission and receipt may be computed as $20 \log_{10}(VRx/VTx)$, where VTx is the transmitted signal voltage (amplitude) and VRx is the received signal voltage (amplitude).

Other signal characteristics may additionally or alternatively be derived.

Deriving the phase angle of a sensed signal may be a standard procedure and the skilled person will be aware of means for implementing this functionality.

Deriving the signal time of flight (transmission time) may be achieved by recording the time of transmission of the signal and the time of receipt of the signal and calculating the difference. For performing this, each of the reference units and the positionable unit may comprise an internal clock and the clocks may be synchronized. Additionally or alternatively, a central controller 36 may track the time of transmission of the signal and receipt of the same signal at a receiver unit. Directly sequential transmission and receipt events may be assumed to be associated with the same signal.

Deriving the path loss (signal attenuation) may be achieved simply by recording the signal strength at transmission (or generating the signal for transmission at a known strength) measuring the strength of the same signal on receipt, and then computing the change. The strength of the signal may refer for example to signal amplitude, e.g. in volts, for example peak-to-peak amplitude. The signal attenuation, or path loss PL, of a signal between transmission and receipt may be computed as $20 \log_{10}(VRx/VTx)$, where VTx is the transmitted signal voltage (amplitude) and VRx is the received signal voltage (amplitude).

Each of the reference units 34 and the positionable unit 32 may comprise signal processing means permitting measurement of the signal strength, e.g. signal amplitude. In this case, each of the units may comprise a clock, and the clocks may synchronized, allowing the transmission and receipt of a given signal to be matched to one another. In particular, directly sequential transmission and receipt events may be assumed to be associated with the same signal. A central controller may comprise signal processing means for measuring the signal strength of signals received at each reference unit, e.g. amplitude, and may be configured to calculate a signal attenuation between transmission and receipt.

Once the one or more signal characteristics have been derived for the signals received at each electrode pair of each reference unit, in preferable examples, at least one differential signal characteristic value may be determined for each reference unit. Differential signal characteristic value may mean a difference in the signal characteristics value as derived for each of two of the electrode pairs 52 of a given reference unit 34.

For example the differential signal characteristic may be one or more of: phase angle difference, signal transmission time (time of flight) difference and signal attenuation (path loss) difference. In each case the difference may be between the value as measured at each of two electrode pairs of a reference unit. The value of the differential signal characteristic for a given reference unit may be determined by the controller 36 for example, or may be determined locally by each reference unit 34.

A differential value may be derived for one or more signal characteristics in respect of each and every combination of electrode pairs comprised by a given receiver unit. These form a set of values and may be compiled for instance in the form of a matrix ('differential matrix'). This set of differential values may provide a unique characterization of the angle of arrival of a given signal, since depending upon the angle at which a signal enters a reference unit, the difference in measured signal characteristics between two fixed pairs of electrodes will change in a consistent manner.

In some examples therefore, determining the angle of arrival may comprise comparing the derived set of differential values for a given reference unit with a dataset of pre-determined differential value sets, each pre-determined set corresponding to a known signal angle of arrival.

Deriving the signal angle of arrival will be described in greater detail below.

As noted, deriving the indication of position of the positionable unit 32 may comprise accessing a reference dataset comprising information indicative of known angles of arrival of signals transmitted between different combinations of the reference units when the reference units are placed against said known regions of the skin.

The reference dataset may take different forms. In a simple example, the reference dataset may comprise a list or table expounding for each reference unit 34 the angle of arrival of signals at that unit if received from the known locations of various of the other reference units, for instance from each of said known locations. This information alone may be used in combination with the derived angles of arrival of signals from the positionable unit to map a relative position of the positionable unit with regards to the reference units, for instance by resolving the derived angle vectors to the known relative angle measurements. Since the real-world position of the units on the body may be known, this in turn may be transformed into a real-world position indication, i.e. indication of a physical location on the body or skin.

According to further examples, the reference dataset may take the form of a device body map for the reference units. This may be representative of relative positioning of the reference units on the body. The body map may be representative of relative body positions of the reference units, for instance as characterized or indicated by signal arrival angles (i.e. relative angular positioning) and preferably also separation distances (e.g. as indicated from relative signal arrival times). The device body map may be represented in the form of co-ordinate positions of the reference units on the body (from which relative angle information may be implicit or may be derived) or may simply be represented in terms of a list of relative distances and angles of each reference unit to each other reference unit. The co-ordinate positions in this case may be in terms of a local body co-ordinate system, i.e. a co-ordinate system of the body 'reference frame'.

Deriving of the indication of position may be performed based on a combination of the reference information in the reference dataset or body map and the derived angles of arrival of the signals at each of the reference units. Known algorithms for deducing a position based on resolving measured angle of arrival information with reference angle of arrival information, for instance using triangulation techniques, are described in detail for instance in the paper: Dash, Shubhra Shubhankari, et al. "A Survey on localization in Wireless Sensor Network by Angle of Arrival." International Journal 2: 115-122.

An indication of an orientation of the positionable unit may also be derived according to one or more examples. For this, the positionable unit may comprise at least two pairs of electrodes for transmitting signals. For deriving orientation, the differential signal characteristics referred to above are particularly useful. This may be because the difference in e.g. time of flight, of a signal between two spaced electrode pairs having fixed positions on the positionable unit will change in a consistent manner in dependence upon the angle or orientation of that unit.

In addition, the set of arrival angles of signals at the electrode pairs of the receiver unit may vary depending upon the position of the electrode pair from which the signals are sent. By virtue of this, different orientations of the positionable unit, having multiple pairs of electrodes mounted at fixed positions, may result in different characteristic sets of arrival angles at the electrode pairs of each of the reference units. This may be used to track orientation. This concept will be explained in greater detail below.

Figure 4:
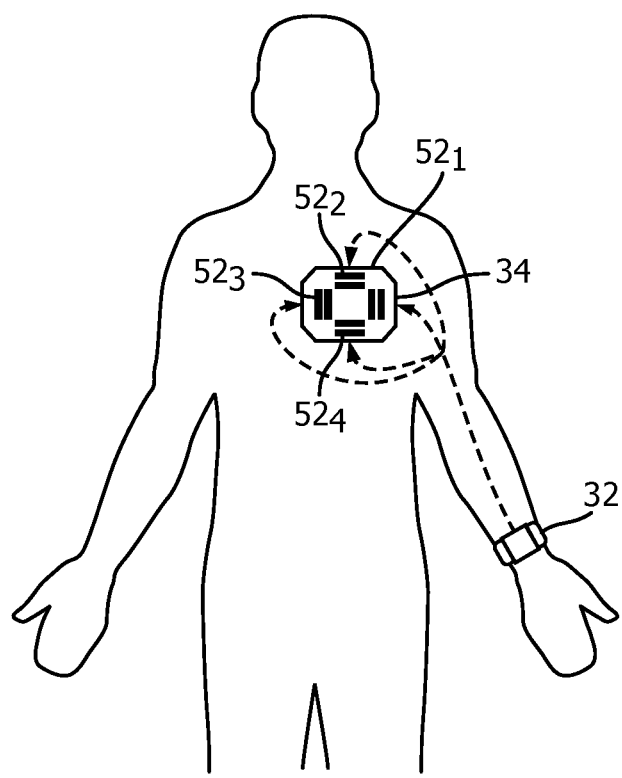
FIG. 4 schematically depicts example on-body sensor system in situ on the body according to an embodiment.

As noted above, in advantageous examples, the system 30 may comprise more than two reference units 34. This permits more precise and reliable determination of the position of a positionable unit. By way of illustration, FIG. 4 schematically illustrates a system comprising three reference units 34a, 34b, 34c. The system is shown in situ, with the positionable unit 32 and reference units positioned in place at various points on the body of a sample subject 70. In this example, the positionable unit may be placed at a central position; with the reference units positioned surrounding the positionable unit. Arrows schematically indicate transmission of signals between the positionable unit and reference units.

The shown configuration is by way of illustration only, and in other examples, any other layout of the components of the system on the body may be chosen. Positioning the positionable unit in a relatively central position within the plurality of reference units may however be advantageous since it aids in the position determination process, in particular if said process uses triangulation techniques.

As mentioned above, handling of signal generation and processing functions may be distributed between components of the system 30 in different ways. For example, signal generation and processing of received signals may be performed centrally by a (central) controller 36, wherein the positionable unit and the reference units are for electrically coupling generated and received signals into and back out from the body. They may each comprise one or more electrodes for facilitating this for instance. As an example, reference units may have one local central controller and the positionable unit a different controller.

Central signal generation may not be used, for instance where the positionable unit and/or the reference units are remote, wireless devices there may not be a transmission path for delivering centrally generated signals. Hence, signal generation and the processing of received signals may be distributed between the skin interface units. For example, the positionable unit 32 may comprise circuitry for generating signals for applying to the body, and the reference units 34 may each comprise circuitry for processing sensed signals.

In further examples, at least the reference units, and optionally also the positionable unit, may each be selectably configurable to perform both a signal transmission function and a signal receiving function. Hence the functionality of the two may be interchangeable. Each may comprise circuitry both for generating signals for coupling into the body and for processing signals coupled back out of the body. Certain of the skin interface units may be switchable between the two modes or functionalities, to thereby increase flexibility of the system, or to permit for instance the reference units to carry out a calibration procedure which requires signal transmission as well as signal sensing. Such a skin interface unit may be termed a multi-function interface unit.

Figure 5:
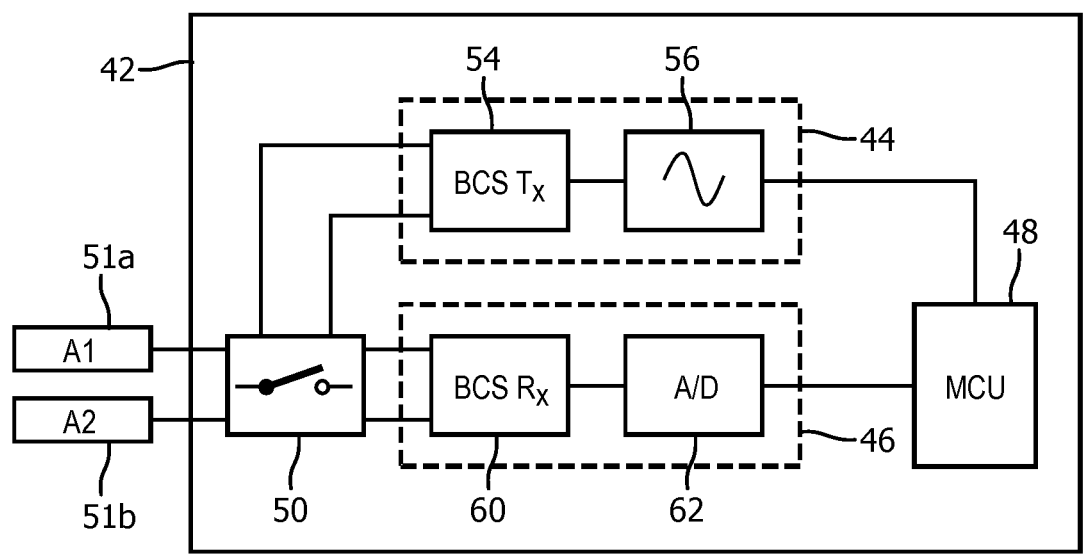
FIG. 5 shows in block diagram form an example signal transceiver as may be used in example systems according to one or more embodiments.

FIG. 5 shows, in block diagram form, circuitry which may be comprised by such a multi-function skin interface unit, to permit implementation of both signal generation (transmission) and processing of received signals.

The circuitry together may form a transceiver unit 42 for controlling generation and transmission of signals through the body via the given skin interface unit, and also for receiving of signals. This transceiver unit may be referred to as an RF unit.

The transceiver unit 42 may include one set of components for controlling signal generation and transmission (transmitter circuit part 44) and a second set of components for controlling receiving of signals (receiver circuit part 46). Both parts may be operatively connected to a microcontroller unit (MCU) which controls the transmitter 44 and receiver 46 parts. Both the transmitter and receiver parts may be connected with a switch 50 which interfaces with pair of skin contacting electrodes 51a, 51b, dubbed electrode A1 and A2. More than one pair of electrodes may be included in further examples. The switch 50 may be for switching the given interface unit 32, 34 between signal transmission mode (which connects the electrodes to the transmitter circuit part 44) and signal receiving mode (which connects the electrodes to the receiver circuit part 46).

The signal transmission part 44 may include a signal generator 56 adapted to generate electrical signals for coupling into the skin by the electrodes 51. The signal generator may generate alternating signals at radio frequencies. Preferably, signals may be generated in a frequency range 10 MHz to 150 MHz as in this frequency range the human body behaves as a waveguide for signal transmission.

The transmitter part 44 may include a voltage booster and driver 54 ('BCS $T_x$') adapted to receive the generated raw signals, amplify (i.e. boost) them and drive application of the signals, via the switch and electrodes 51, to the body.

The signal receiver part 46 may include an analog front end element 60 ('BCS $R_x$') for receiving in analogue form, via the switch 50, the raw signals sensed by the electrodes 51. The front end element may communicate the received signals to an analogue-to-digital converter 62 ('A/D') which processes the signals and outputs them in digital form to the microcontroller unit 48.

In other examples, each of the skin interface units 32, 34 may be configured to perform only one of signal generation or signal sensing. In particular the positionable unit may be for signal transmission and the reference units for signal receiving. In this case, each may comprise only one of the transmitter 44 or receiver 46 circuit parts shown in FIG. 5, and the switch may be omitted. For instance, the positionable unit 32 may comprise only the transmitter circuit part 44, and the reference units 34 may comprise only the receiver circuit part 46.

In further examples, both the transmitter 44 and receiver 46 circuit parts of the transceiver unit 42 shown in FIG. 5 may be comprised by the central controller 36, with the controller 36 configured to electrically communicate signals to and from the skin interface units 32, 34.

Embodiments of the invention involve determining an angle of arrival of signals at the reference units. This process will now be described in more detail with reference to FIGS. 6 to 10.

Figure 6:
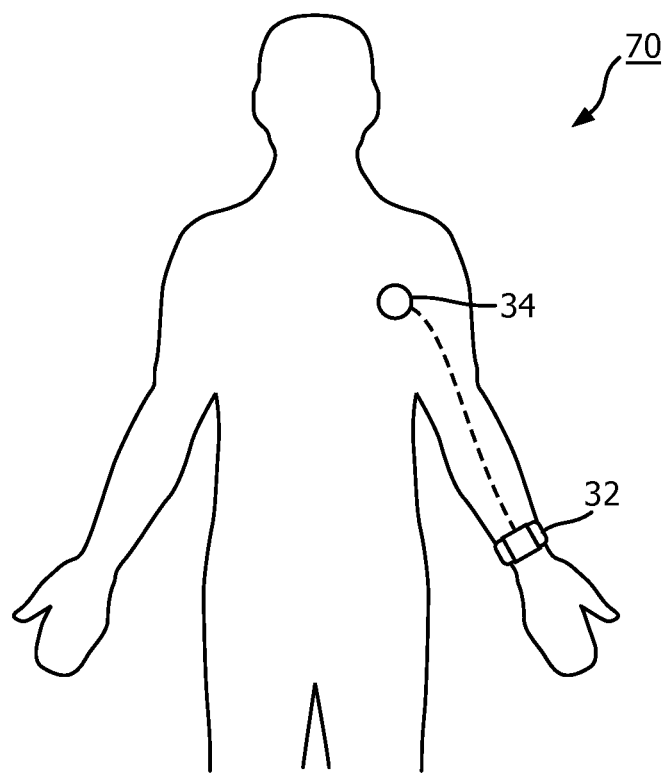
FIGS. 6, 7, 8, 9 and 10 schematically illustrate processes and component arrangements for determining an angle of arrival of a signal.

For purposes of illustration, FIG. 6 first shows a sample arrangement comprising a single positionable unit 32 and a single reference unit, each comprising only a single pair of electrodes 52. For purposes of simplicity the electrode pair may be schematically depicted as a single rectangle.

Since there may be only one pair of electrodes 52 comprised by the reference unit, it may not be possible to derive a differential value of any signal characteristic, i.e. the difference in the value between two pairs of electrodes. Hence, no phase angle difference, time of flight (ToF) difference or comparison of path loss may be calculated for example. Without the ability to derive signal characteristics at two different electrode pairs, it may not be possible to calculate an angle of arrival (AoA) of a signal at the reference unit 34.

The only measurements which may be made are absolute measurements of one or more signal characteristics, for example the absolute ToF value or path loss value between the positionable unit 32 and the reference unit 34. From this may be derived a circle of possible positions at which the reference unit may lie (or a surface of a sphere in three dimensions). However, more specific localization may not be possible.

Figure 7:
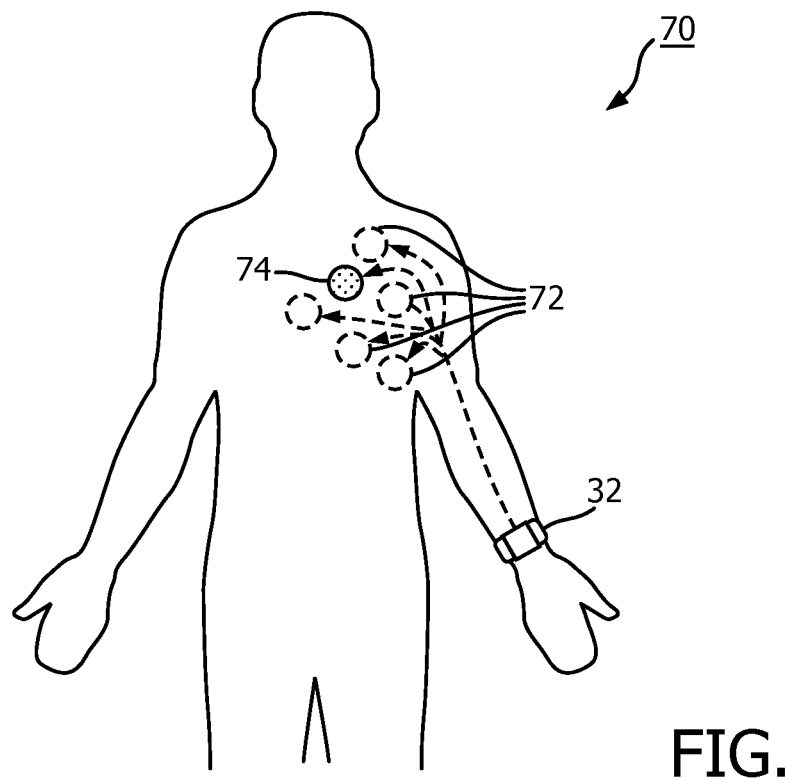

By way of contrast, FIG. 7 schematically depicts an example arrangement comprising a single positionable unit 32 and a single reference unit 34, wherein the reference unit comprises two electrode pairs 52a, 52b. The positionable unit 32 is shown in a number of different example positions around the reference unit, labelled I, J, K, and L.

When the positionable unit is in location I, the phase angle difference between the two receiver electrodes 52a and 52b, which may be expressed as Øa-Øb, will be positive and at a maximum value (assuming the electrodes are within a single a wavelength of one another).

If the positionable unit may be moved from location I to location J, the measured phase angle difference Øa-Øb will continually reduce as location J is approached. This may be because the disparity in distance between the positionable unit and each of the electrodes 52a, 52b of the reference unit reduces. At location J, the phase angle difference Øa-Øb reaches zero, as the distance between each electrode 52a, 52b of the reference unit and the positionable unit equalizes.

As the positionable unit is moved from Location J to Location K, the value Øa-Øb turns negative and reaches a maximum (negative) value at location K, where the magnitude of the negative phase angle difference will be the same as the positive maximum value reached at location I.

In a similar fashion, time of flight difference may also be calculated between the two electrodes 52a, 52b. This may be expressed as ToFa-ToFb. This value reduces (from a positive maximum at location I) to a minimum value of zero at location J. This again may be because as the positionable unit 32 is moved from location I to location J, the distance between the each of the two electrodes 52a and 52b and the positionable unit electrode 52 becomes equal. As the transmitter moves from Location J to Location K, the value ToFa-ToFb turns negative and reaches a maximum value at location K, which value will have the same magnitude as the positive maximum value reached at location I.

By way of example, a further signal characteristic parameter may additionally or alternatively be used following the same approach. This is known as the path loss difference method.

The path loss PL of a signal between transmission and receipt may be computed as $20 \log_{10}(VRx/VTx)$, where VTx is the transmitted signal voltage (amplitude) and VRx is the received signal voltage (amplitude).

The path loss at the first electrode 52a of the reference unit 54 is given by $PLa=20 \log_{10}(VRx\_a/VTx)$, where VRx_a is the signal voltage received at the reference unit electrode 52a and VTx is the signal voltage initially transmitted from the positionable unit electrode 52.

As the positionable unit 52 moves from location I to location J, PLa-PLb increases from a negative maximum at location I to a value of zero at location J. This may be due to equalizing distance between each of the electrodes 52a and 52b of the receiver unit and the positionable unit electrode 52. At location J, the distance is equal.

As the positionable unit 52 may be moved from Location J to Location K, the value PLa-PLb turns positive and reaches a maximum value at location K, where the magnitude of the value may be the same as the positive negative value reached at location I.

Using two electrode pairs as in the example arrangement of FIG. 7, it may not be possible to determine whether the positionable unit is placed above or below the line of symmetry 72 indicated by the dashed line in FIG. 7. The scope of precision or the resolution of the angle determination may be restricted to a scope of 180°; it may be determined at what angle the signal arrives relative to a notional horizontal of the reference unit 34, from 0-180°, but not whether it arrives from the front or the back of the unit.

The precision of the angle of arrival measurement may be constrained by the achievable resolution of the phase angle measurement (or ToF difference or PL difference). Hence increasing resolution of the phase angle difference measurement permits greater precision in the derived angle of arrival (AoA).

Figure 8:
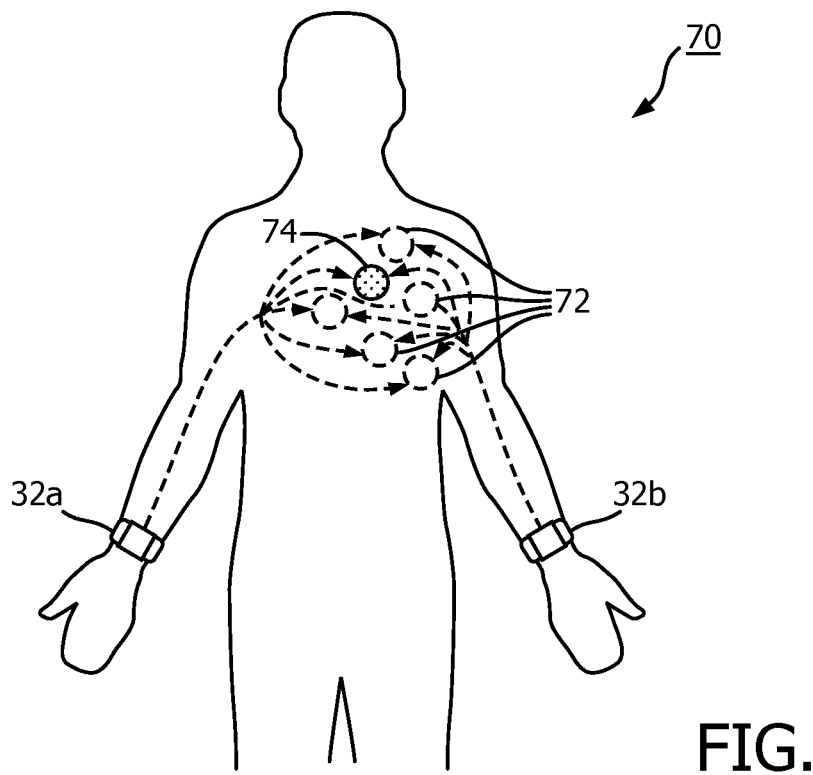
Figure 9:
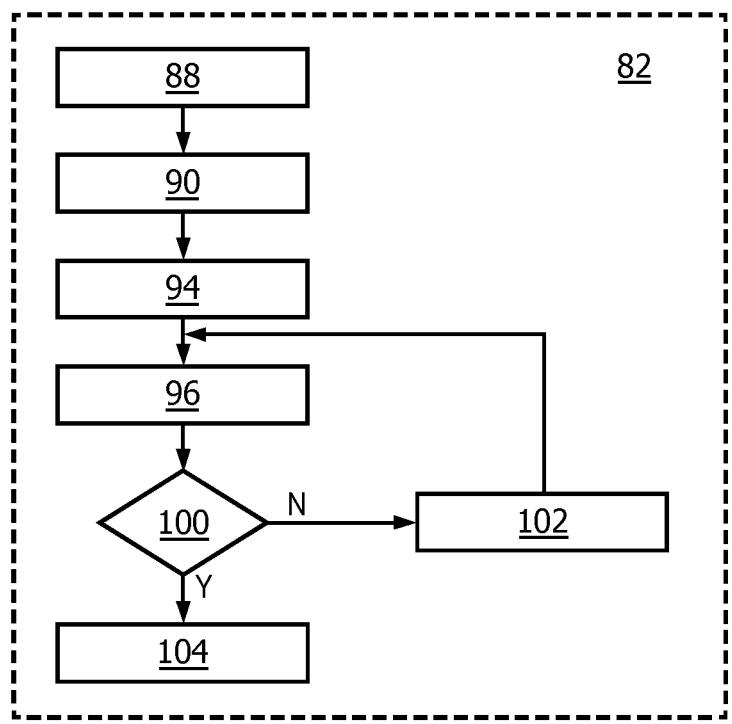

FIG. 8 and FIG. 9 schematically depict example arrangements comprising a reference unit having three electrode pairs and four electrode pairs respectively.

With three or more electrode pairs, it may be possible to uniquely identify the AoA of a body channel signal from a transmitter towards a given receiver.

An example technique for deriving AoA will now be outlined with reference to an example arrangement having a reference unit comprising three electrode pairs. However, the same approach may be equally applicable to any larger number of electrode pairs.

The pairwise phase angle differences between three electrode pairs 52a, 52b, 52c may be expressed by Øa-Øb, Øa-Øc, Øb-Øc, which will be denoted respectively by $Ø_{AB}$, $Ø_{AC}$ and $Ø_{BC}$.

With reference to FIG. 8, it may be recognized that when the transmitter is located at location L, $Ø_{AB}=0$, and $Ø_{AC}$ and $Ø_{BC}$ will be maximum and positive. As the transmitter moves from location L to location I, $Ø_{AB}$ reaches maximum positive value while $Ø_{AC}$ and $Ø_{BC}$ will be equal in magnitude and opposite in sign. At location J, $Ø_{AB}=0$ while $Ø_{AC}$ and $Ø_{BC}$ will be maximum and negative. And at location K, $Ø_{AB}$ reaches maximum negative value while $Ø_{AC}$ and $Ø_{BC}$ will be equal in magnitude and opposite in sign.

A similar approach may also be applied for other signal characteristics, including ToF based computation and Path Loss based computation (although note that the path loss method results in opposite sign with respect to phase angle difference and ToF difference methods).

Using this approach, the directionality of a received signal in terms of angle of arrival (AoA) at the receiver unit 34 may be uniquely characterized by a respective set of values of $Ø_{AB}$, $Ø_{AC}$ and $Ø_{BC}$. Each AoA has a unique set of differential parameter values $Ø_{AB}$, $Ø_{AC}$ and $Ø_{BC}$. This provides a means of determining AoA of a given signal with a scope of precision of 360°, by calculating the set of differential values and comparing it for example with stored reference value sets corresponding to different possible angles of arrival.

By way of further explanation, a phase angle difference matrix may be defined for a given reference unit, which for a unit having n electrode pairs may be expressed as $$\phi_{diff} = \begin{bmatrix} \phi 11 & \cdots & \phi 1n \\ \vdots & \ddots & \vdots \\ \phi n1 & \cdots & \phi nn \end{bmatrix}$$

for every location of the receiver. Where $Ø_{ij}$ is the phase angle difference between signal received at electrode pair i and electrode pair j respectively. Note that $Ø_{ii}=0$.

Similarly, a ToF difference matrix for a receiver unit comprising n electrode pairs may be defined and expressed as $$ToF_{diff} = \begin{bmatrix} ToF11 & \cdots & ToF1n \\ \vdots & \ddots & \vdots \\ ToFn1 & \cdots & ToFnn \end{bmatrix}$$

where $\text{ToF}_{ij}$ is the difference between the derived time of flight of the signal received at electrode pair i and electrode pair j respectively. Note that $\text{ToF}_{ii}=0$.

Similarly again a path loss (PL) difference matrix may be defined for a receiver unit comprising n electrode pairs and may be expressed as $$PL_{diff} = \begin{bmatrix} PL11 & \ldots & PL1n \\ \vdots & \ddots & \vdots \\ PLn1 & \ldots & PLnn \end{bmatrix}$$

where $PL_{ij}$ is the difference in the derived path loss of the signal received at electrode pair i and electrode pair j respectively. Note that $PL_{ii}=0$.

Preferably, after deriving such a matrix of differential values, the matrix values are normalized by the maximum value in the matrix. Accordingly, the ratio $\emptyset_{diff}/\emptyset_{max}$, $\text{ToF}_{diff}/\text{ToF}_{max}$ and $PL_{diff}/PL_{max}$ are calculated, where $\emptyset_{max}$, $\text{ToF}_{max}$, $PL_{max}$ denote the maximum value in the phase angle difference matrix, ToF difference matrix and path loss difference matrix respectively.

This normalization ensures that the matrix differential values are all numerical values which may be mapped to a particular AoA. In other words, it allows a standard set of (normalized) differential value matrices to be defined, each corresponding to a known AoA, and where measured matrices may be reliably or faithfully compared with these standard values regardless of the particular physical dimensions or operating parameters of the system.

Normalization also makes the AoA computation robust to change in body channel properties which may occur. Note that other normalization factors may be used to achieve the same results, and further examples will be apparent to the skilled person.

Each signal AoA at the reference unit 34 from the positionable unit may be mapped to a unique $\emptyset_{diff}/\emptyset_{max}$, $\text{ToF}_{diff}/\text{ToF}_{max}$ and $PL_{diff}/PL_{max}$.

As noted, a dataset of pre-determined differential value matrices may be constructed, each predetermined matrix corresponding to a single known signal angle of arrival at the reference unit. A common dataset may be used for all reference units, so long as each has the same spatial configuration of electrodes.

Derived differential value matrices (preferably after normalization) may then be compared with the matrices in pre-determined dataset to thereby uniquely map the corresponding AoA of the given signal.

Figure 10:
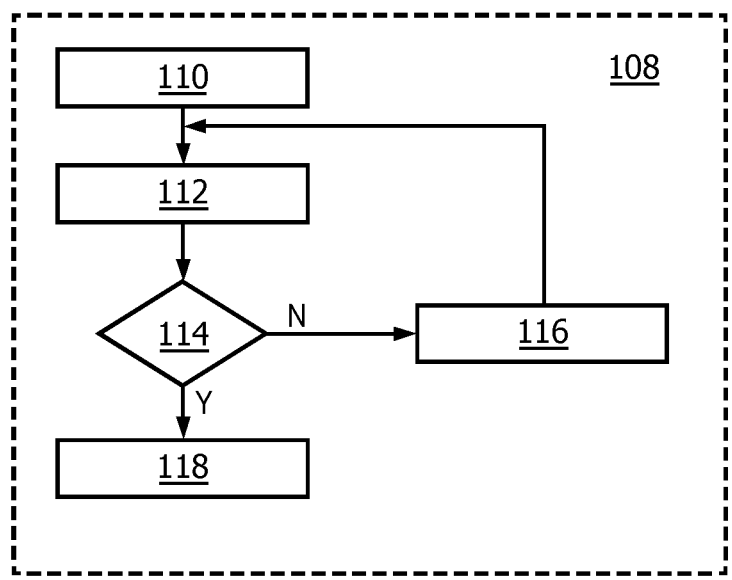

According to certain examples, the positionable unit 32 may comprise more than one electrode pair. FIG. 10 schematically depicts an example arrangement in which both the positionable unit and an example reference unit 34 comprise four electrode pairs each. In this case, each electrode pair in the positionable unit may be sequentially controlled to transmit signals towards the reference unit(s). This may be controlled by a central controller 36 or control may be implemented for example via reciprocal communication between the positionable unit and the reference unit, for instance using wireless communication means.

For each transmitting electrode pair, it may be possible to derive a respective set of $\emptyset_{diff}$, $\text{ToF}_{diff}$ and $PL_{diff}$ matrices for the reference unit 34. These may be denoted by $\emptyset_{diff\_K}$, $\text{ToF}_{diff\_K}$ and $PL_{diff\_K}$ for the Kth transmitting electrode pair. A total of n sets of $\emptyset_{diff}$, $\text{ToF}_{diff}$ and $PL_{diff}$ matrices may be derived for a total set of n transmitting electrodes of a positionable unit.

This allows a separate angle of arrival to be derived in respect of each transmitting electrode, for instance by comparing each matrix set to a pre-determined reference set of matrices as discussed above, each corresponding to a known AoA.

This then also allows an orientation of the positionable unit to be derived as the set of AoA values for the two or more transmitting electrode pairs will vary depending upon the orientation of the positionable unit to which they are mounted. In particular, known sets of two or more AOA values for the two or more transmitting electrode pairs may be included in the reference dataset, each set corresponding to a known possible orientation of the positionable unit. When a set of AOA values is derived for a positionable unit, it may be compared with the sets in the reference data set to determine which orientation the positionable unit is placed in.

An indication of the position of each separate transmitting electrode may be derived in accordance with procedures outlined above and below in greater detail, and based on, and a known spatial arrangement of the electrodes on the positionable unit, an orientation of the unit may be derived.

Embodiments of the various systems, devices, and/or methods described herein may make use of a reference dataset comprising information indicative of known angles of arrival of signals transmitted between different combinations of the reference units when the reference units are placed against said known regions of the skin.

Additionally, a method of calibrating or configuring an on-body sensor system to thereby construct this reference dataset for subsequent use in localizing the positionable unit may be provided. This will now be described in more detail.

These systems, devices and/or methods may provide a method of calibrating an on-body sensor system for determining position of a skin interface unit of the system, the system comprising:
a plurality of skin interface units for coupling electrical signals into and/or out of the body of a subject, including two or more reference units, each for placement against a respective known region of the skin, and at least one positionable unit for placement at a further unknown position, each of the reference units comprising at least two pairs of skin coupling electrodes, the method comprising:
positioning the two or more reference units against said respective known regions of the skin;
sequentially controlling each of the reference units to transmit signals into the body toward the other reference units and in each case deriving at one or more other reference units one or more signal characteristics associated with signals received at each electrode pair respectively of the other unit, and deriving based on this an indication of an angle of arrival of the signals at each of said reference units;
generating and storing a dataset of information indicative of the derived angles of arrival of signals transmitted between the reference units, the dataset for use as a reference in subsequently deriving indications of position of the at least one positionable unit based on angles of arrival of signals transmitted between the positionable unit and the reference units.

The reference units used may the same reference units used by the system to perform position determination, or may be a separate set of reference units. The separate set should be each configured to perform both signal transmission and signal sensing. The reference units for position determination are required only to perform signal sensing.

Figure 11:
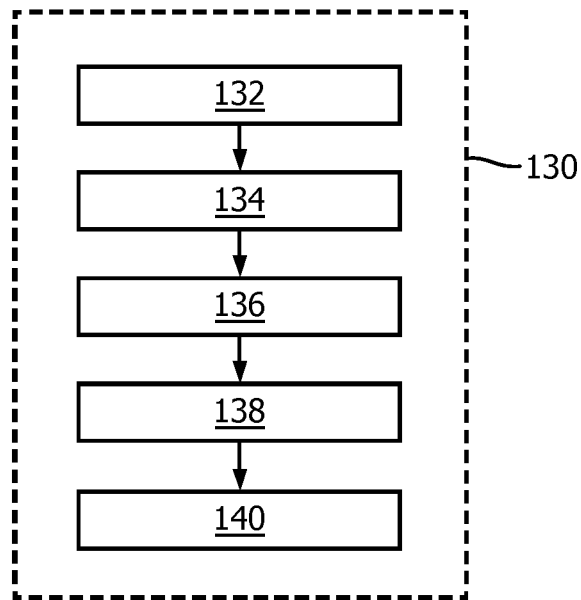
FIG. 11 shows in block diagram form an example method for calibrating an on-body sensor system.

An example calibration method 80 will now be described with reference to FIG. 11, which shows the example method in block diagram form.

In a first step 86, the plurality of reference units 34 of the system may each be positioned against a respective predetermined and known region of the skin of the patient's body. They may be mounted or fixed to the body, or may in some cases simply be placed against the body, e.g. in the case of a reference unit in the form of a smart weight scale or handheld device, where the subject simply comes in contact with the device, e.g. stands on the scale or the handheld device may be placed against the subject.

According to an optional second step 88, one of the reference units 34 may be configured to operate as a control unit for coordinating the calibration procedure, and the remaining reference units are configured to operate as slave units operably coupled (e.g. wirelessly) with the control reference unit. This step may be omitted in the case that a central controller 36 may be provided for controlling the calibration procedure. In the remaining steps, reference to controller may be understood as referring either to a central controller or to one of the reference units configured to act as a controller.

The reference units 34 may establish 90 or initialize wireless communication with the controller, and preferably also with one another.

The controller then may configure 92 one of the reference units 34 in a transmitting mode, and the other reference units 34 in a receiving mode.

The transmitting reference unit may be controlled 94 to couple generated electrical signals into the body to thereby transmit electrical body channel signals through the body toward the other receiving reference units. If the transmitting reference unit comprises more than one pair of electrodes, each pair may be controlled sequentially in turn to transmit signals into the body toward the other units.

For each of the receiving reference units, one or more signal characteristics associated with signals received at each electrode pair respectively of the unit are derived, and based on this an indication of an angle of arrival of the signals at each of said other reference units may be derived 96. This may be then stored, either at each respective reference unit or centrally at the controller.

Steps 92-96 may be repeated for each of the reference units, each one being configured in turn in transmitting mode and the remaining reference units configured in receiving mode. Angles of arrival of signals from each reference unit at each and every other reference unit are hence derived, and these are then collected centrally 98 at the control unit. For instance the reference units may each communicate locally stored AoA data to the control unit, or the data may be retrieved from storage at the control unit. Based on the information the control unit generates and stores a dataset of information indicative of the derived angles of arrival of signals transmitted between the reference units.

The dataset may in some examples be in the form of a device body map for the reference units, representative of relative positioning of the reference units on the body. This may be constructed based solely on the angle of arrival information, and be representative of relative angular positioning. Optionally, the calibration method may further include collecting signal arrival time information and based on this deriving a relative separation of each reference unit from each other reference unit. This may allow a device body map to be constructed which includes more exact relative position information for the reference units.

The device body map may contain or comprise co-ordinate positions of the reference units. Relative angular positioning of the reference units may be implicit in this or may be derived from it. The co-ordinate positions may in some examples be co-ordinate positions in terms of a local body co-ordinate system, e.g. a co-ordinate system relative to the body frame of reference.

Methods for deriving angle of arrival of a signal have been described in detail above.

Embodiments described herein may include a method for determining a position of at least one skin interface unit of an on-body sensor system. The system in this case comprises a plurality of skin interface units for coupling electrical signals into and/or out of the body of a subject, including two or more reference units 34a, 34b, each for placement against a respective known region of the skin, and at least one positionable unit 32 for placement at a further unknown position, wherein each of the reference units comprises at least two pairs 52 of skin coupling electrodes.

The method may comprise:
controlling transmission of signals through the body between the positionable unit and the reference units;
deriving at each reference unit one or more signal characteristics associated with signals received at each pair of electrodes respectively of the unit, and based on this deriving an indication of an angle of arrival of the signals at the reference unit;
accessing a reference dataset comprising information indicative of known angles of arrival of signals at reference units if placed at said known regions of the skin, and if received from locations corresponding to one or more of said other known regions of the skin; and
deriving an indication of position of the at least one positionable unit based on the derived angles of arrival of signals and on the information in the reference, and generating output information based on the derived indication of position.

Although the system is assumed to include a controller, the controller may be one of the skin interface units in one or more examples, the relevant unit being configured to perform the control functions associated with the controller. Which unit acts as controller may be determined by the system at the start of the method for example. References to the controller may be understood as referring either to a central controller or a controller as implemented by one of the skin interface units.

Figure 12:
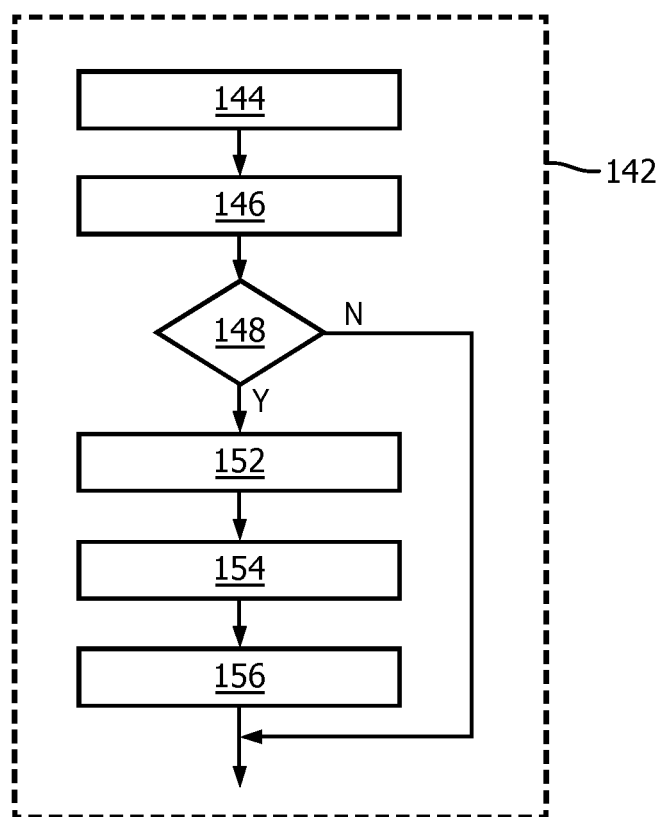
FIG. 12 shows in block diagram form an example method of determining placement of skin interface units of an on-body sensing system.

An example method 100 for determining position indication of a positionable unit is shown in block diagram form in FIG. 12.

In a first step 102 of the method, the positionable unit 32 may be positioned on the body of the subject, for example by the subject, a caregiver, and/or a medical professional. The reference devices may also be positioned on the body at a known set of reference locations in this step, or this may have been already performed in advance of the present method. In some examples, the positionable device may require configuring in signal transmission mode, if it has transmission and sensing modes for example. The controller 36 may perform this or a user may perform this. The reference units 34 may need configuring in signal receiving mode if they similarly have transmission and receiving modes. Again this may be performed by a controller or by the user in different examples.

The positionable unit 32 then may be controlled 104 by the controller 36 to couple electrical signals into the body for transmitting the signals through the body toward the plurality of receiver units 34. If the positionable unit comprises more than one pair of electrodes, each pair may be controlled in turn to transmit signals toward the receiver units.

Coincident with transmission, the receiver units 34 may be controlled to sense signals received at each electrode pair and for each pair 52 of electrodes there may be determined 106 one or more signal characteristics associated with the signals received at that pair. Procedures for determining the signal characteristics have been described above in relation to the system aspect. This may be performed by the controller or locally by the respective reference unit 34.

Based on the signal characteristics at the two or more pairs of electrodes, an indication of an angle of arrival of the signal may be derived 108. Procedures for determining the angle of arrival have been described in detail above, for instance with reference to FIGS. 6-10. Where one of the reference units 34 is configured to act as a control device (as described above), the derived angles of arrival for each reference unit may be communicated by the reference units to the controller unit. They may be communicated to a separate central controller 36 unit.

The controller unit (central or distributed) may access 110 a reference dataset, for instance in the form of a device body map comprising information indicative of relative spatial positioning of the reference units relative to one another, including relative angular positioning in terms of known angles of arrival of signals when transmitted between different of the reference units.

Based on information in the dataset or body map, and on the derived angles of arrival of the signals at each of the reference units 34 from the positionable unit 32, an indication of position of the positionable device on the body may be derived 112. Output information may be generated based on this derived position indication, for instance indicative of the derived position indication.

Known algorithms for deriving the indication of position such as triangulation methods are described in detail for example in the paper Dash, Shubhra Shubhankari, et al. "A Survey on localization in Wireless Sensor Network by Angle of Arrival." International Journal 2: 115-122.

Examples, options, embodiments and variations described above in relation to the system 30 aspect of this invention may applied equally to the above defined method 100 according to examples.

According to one set of examples the position determination method 100 may include as an initial calibration stage a calibration procedure in accordance with one of the example calibration methods 80 described above. The configuration method 100 may hence in this case be a two-stage method, comprising as a first stage a calibration procedure 80 as defined in any of the examples outlined above (for instance as described with reference to FIG. 11) and as a second stage a position determination procedure comprising the steps (e.g. 102-112) outlined in the immediately preceding passages, and as shown in FIG. 12.

Whilst the above embodiments of the invention are described in the form of a patch it is clear that they may also be advantageously applied to handheld devices which are contacted with the body, as described throughout this disclosure. An example of such a class of device is a hand held imaging sensor and in particular a hand held ultrasound device, which may comprise a cMUT array for image acquisition.

As discussed above, embodiments make use of a controller. The controller may be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon may be loaded into a processor or controller.

Variations to the disclosed embodiments may be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An on-body sensor system comprising:
   a plurality of skin interface units, the plurality of skin interface units comprising two or more reference units, each for placement against a respective known region of the skin, and at least one positionable unit for placement at a further unknown position, wherein each of the reference units comprise at least two pairs of skin coupling electrodes; and
   a controller operably coupled with the skin interface units for
      controlling transmission of signals through the body of the subject between the positionable unit and the reference units,
      deriving, at each reference unit, one or more signal characteristics associated with signals received at each pair of electrodes respectively of the unit,
      deriving, based on the one or more signal characteristics, an indication of an angle of arrival of signals at the reference unit,
      accessing a reference dataset comprising information indicative of known angles of arrival of signals at reference units if placed at said known regions of the skin, and if received from locations corresponding to one or more of said other known regions of the skin, and deriving an indication of position of the at least one positionable unit based on the derived angles of arrival of signals and on the information in the reference dataset, and generating output information based on the derived indication of position.

2. The on-body sensor system as claimed in claim 1, wherein the one or more signal characteristics include at least one of: phase angle, signal transmission time, or a signal attenuation between transmission and receipt.

3. The on-body sensor system as claimed in claim 1, wherein each reference unit comprises at least three pairs of skin-coupling electrodes.

4. The on-body sensor system as claimed in claim 3, wherein for each reference unit the controller determines at least one differential signal characteristic value based on a difference in the value of a signal characteristic between two of the pairs of electrodes.

5. The on-body sensor system as claimed in claim 4, wherein for each reference unit, and for at least one signal characteristic, a differential signal characteristic value is calculated between each electrode pair and each other electrode pair comprised by the receiver, to thereby form a set of differential values.

6. The on-body sensor system as claimed in claim 5, wherein the derived set of differential values is normalized by dividing each value in the set by the maximum differential value contained in the set.

7. The on-body sensor system as claimed in claim 5, wherein determining the angle of arrival comprises comparing the derived set of differential values with a dataset of pre-determined differential values sets, each predetermined set corresponding to a known signal angle of arrival.

8. The on-body sensor system as claimed in claim 1, wherein the indication of position is determined based on a triangulation technique.

9. The on-body sensor system as claimed in claim 1, wherein the reference dataset comprises a device body map for the reference units, representative of relative positioning of the reference units on the body.

10. The on-body sensor system as claimed in claim 1, wherein the controller:

identifies the number of electrode pairs comprised by the positionable unit, controls transmission of signals by each electrode pair in turn to each of the reference units, and derives, at each reference unit, a separate set of signal characteristics associated with the signals transmitted from each electrode pair.

11. The on-body sensor system as claimed in claim 1, wherein each of the reference units is operable as both a signal transmitter and signal receiver.

12. A method of determining placement of skin interface units of an on-body sensing system, wherein the system comprises a plurality of skin interface units, including two or more reference units, each for placement against a respective known region of the skin, and at least one positionable unit for placement at a further unknown position, each of the reference units comprising at least two pairs of skin coupling electrodes; and the method comprising:

controlling transmission of signals through the body between the positionable unit and the reference units;

deriving at each reference unit one or more signal characteristics associated with signals received at each pair of electrodes respectively of the unit, and, based on the one or more signal characteristics, deriving an indication of an angle of arrival of the signals at the reference unit;

accessing a reference dataset comprising information indicative of known angles of arrival of signals at reference units if placed at said known regions of the skin, and if received from locations corresponding to one or more of said other known regions of the skin; and deriving an indication of position of the at least one positionable unit based on the derived angles of arrival of signals and on the information in the reference dataset, and generating output information based on the derived indication of position.

13. The method as claimed in claim 12, the method further comprising determining at least one differential signal characteristic value based on a difference in a signal characteristic value between two of the pairs of electrodes.

14. The method as claimed in claim 13, the method comprising, for each reference unit, and for at least one signal characteristic, calculating a differential signal characteristic value between each pair of electrodes and each other pair of electrodes comprised by the reference unit, to thereby form a set of differential values.

\* \* \* \* \*